United States Patent [19]
Gunata et al.

[11] Patent Number: 6,087,131
[45] Date of Patent: Jul. 11, 2000

[54] β-GLUCOSIDASE FROM FILAMENTOUS FUNGI, AND USES THEREOF

[75] Inventors: Yusuf Ziya Gunata; Marie-José Vallier, both of Montpellier; Raymond Baumes, Saint-Clement-de-Riviere; Claude Bayonove, Montpellier, all of France

[73] Assignee: Institut National de la Recherche Agronomique - I.N.R.A., Paris, France

[21] Appl. No.: 08/973,867

[22] PCT Filed: Jul. 5, 1996

[86] PCT No.: PCT/FR96/01054

§ 371 Date: Jan. 6, 1998

§ 102(e) Date: Jan. 6, 1998

[87] PCT Pub. No.: WO97/02341

PCT Pub. Date: Jan. 23, 1997

[30] Foreign Application Priority Data

Jul. 6, 1995 [FR] France .................................. 95/08185

[51] Int. Cl.[7] .............................. C12P 19/44; C12P 1/02; C12N 1/38; A23L 2/00

[52] U.S. Cl. .................................. 435/74; 435/72; 435/99; 435/171; 435/209; 435/254.1; 435/244; 426/590

[58] Field of Search .................................. 435/201, 254.1, 435/209, 72, 74, 99, 244, 171; 426/590

[56] References Cited

PUBLICATIONS

Derwent Caplus ACS 1997:87700 Mallozzi et al "Effect of flavonoids on *Aspergillus flavus* growth and aflatoxin production" Rev. Microb. (1996, 27 (3) pp. 161–165.

Derwent Caplus ACS 1970:506534 Haluk et al Bull Soc. Chim Biol (1970) 52, (6) pp. 667–677.

*Primary Examiner*—Herbert J. Lilling
*Attorney, Agent, or Firm*—Oblon, Spivak, McClelland, Maier & Neustadt, P.C.

[57] ABSTRACT

An acid-stable β-glucosidase that may be prepared from filamentous fungi and has very low glucose inhibition sensitivity is disclosed. Said β-glucosidase is particularly useful for preparing fruit juices and in enzymatic cellulose hydrolysis methods.

12 Claims, 4 Drawing Sheets

β-GLUCOSIDASE FROM FILAMENTOUS FUNGI, AND USES THEREOF

The present invention relates to a β-glucosidase of fungal origin whose activity is weakly inhibited in the presence of high glucose levels, as well as to the method for producing it, and to its uses.

The β-D-glucoside glucohydrolases (EC 3.2.1.21) commonly called β-glucosidases catalyze the hydrolysis of alkyl- and aryl-β-D-glucosides, as well as that of cellobiose. The use of these enzymes has been proposed in various fields.

It has in particular been proposed to use β-glucosidases for the hydrolysis of nonodorous glycoside precursors of odorous molecules. Indeed, in a large number of fruits such as grapes [WILLIAMS et al., American Chemical Society, Washington, D.C., 35–48, (1989), GUNATA et al., J. Chromatogr., 331, 83–90, (1985)], apricot, peach, apple, passion fruit [KRAMMER et al., J. Agric. Food Chem., 39, 778–781, (1991)], a very high proportion of the molecules responsible for the flavor (terpenols, C13 norisoprenoids, phenols) are bound to sugars, in a nonodorous form.

The sugar part of these glycosides has, for example, been described in the case of grape berries [WILLIAMS et al., Phytochemistry, 21, 2013–2030, (1982)]; VOIRIN et al., J. Chromatogr. 592, 269–281 (1992)]. Present therein are β-D-glucosides, rutino-sides (6-O-α-L-rhamnopyranosyl-β-D-glucopyranosides), 6-O-α-L-arabinofuranosyl-β-D-glucopyranosides and 6-O-β-D-apiofuranosyl-β-D-glucopyranosides. In grapes, as well as in other fruits, the aglycone is always bound to glucose, whether in the case of mono- or of diglycosides.

The glycosidic precursors constitute a substantial part of the flavor potential in fruits, because the proportion of sugar-bound flavor is often greater than the proportion of corresponding free flavor [GUNATA et al., J. Chromatogr. 331, 83–90, (1985); KRAMMER et al., J. Agric. Food Chem. 39, 778–781, (1991)].

Previous studies carried out by the Inventors' team at the Flavor and Natural Substances Laboratory at the Institute of Grapevine Products, INRA of Montpellier, have made it possible to elucidate the mechanism of enzymatic hydrolysis of the glycosidic precursors of grape berry flavor. The terpenic diglyco-sides are hydrolyzed in two stages: in a first stage, α-L-rhamnopyranosidase, or an α-L-arabinofuranosidase, or a β-D-apiofuranosidase, cuts the glycoside bond (1→6) and liberates the corresponding monoglucoside. A β-D-glucopyranosidase is then used to liberate the aglycone from the monoglucosides formed. In the case where the substrate contains only monoglucosides, the hydrolysis is carried out directly without requiring the first stage.

Knowledge of this mechanism and of the properties of the enzymes involved have made it possible to develop a method for producing flavors from their glycosidic precursors, which is the subject of patent application EP 9,001,545, and the production of enzymatic preparations of fungal (particularly *Aspergillus niger*) origin which are capable of liberating flavor molecules from glycosides [GUNATA et al., Progress in Flavour Precursor Studies, SCHREIR, P., WINTERHALTER, P., Eds, Allured: Weaton (USA),219–234, (1993); GUNATA et al., J. Inter. Sci. Vigne Vin 24, 3, 133–143, (1990)].

The use of β-glucosidase may also make it possible to make other improvements to the organoleptic qualities of products derived from fruits: this is the case for citrus juices, whose bitterness is attributed in part to a glycoside (naringin=naringenin-7-rhamnosylglucoside). Hydrolysis by the successive action of an α-rhamnosidase and of a β-glucosidase makes it possible to eliminate this bitterness.

However, the β-glucosidase activity of fungal origin such as that of *A. niger* is strongly inhibited by glucose [WOODWARD and WISEMAN, Enzyme Microbio. Technol. 4, 73–79, (1982); GUNATA et al., Progress in Flavour Precursor Studies; SCHREIER, P., WINTERHALTER, P., Eds, Allured: Wheaton (USA), 219–234, (1993)].

This limits its use for the treatment of products containing glucose, such as fruit juices, or certain wines (natural sweet wines, for example).

Applications of β-glucosidases have also been proposed in other fields, such as for example the hydrolysis of toxic cyanogenetic glucosides contained in certain plants such as cassava, the synthesis of alkyl glucosides used in the pharmaceutical and food industries as nonionic biological surfactants and detergents.

It has also been proposed to use β-glucosidases for the recycling of cellulose.

Cellulose is present in the cell wall of plant tissues, either in a free form, or in the form of lignocellulose or hemicellulose; it represents a very substantial part of the waste from industries which use raw materials of plant origin.

The recycling of cellulose obtained from waste of plant origin involves two successive and distinct stages: a first stage consists of saccharification, that is to say the production of glucose, which can be metabolized by industrial microorganisms, allowing, in the second stage, the bioconversion of the glucose to a source of energy, such as ethanol, or to a protein biomass intended as animal feed.

The enzymatic methods of saccharification are preferred to chemical methods; however, for the method to be profitable, the yield of conversion of cellulose to glucose should be high. Now, during saccharification, the accumulation, in the medium, of cellobiose, a disaccharide formed under the action of cellulases (exo- and endo-1,4-β-D-glucanases) from cellulose, inhibits the latter enzymes. The hydrolysis of cellobiose by a β-glucosidase as it is formed avoids its accumulation in the medium and makes it possible to increase the rate of saccharification.

Among the microorganisms, *Trichoderma reesei* is the most widely used for the production of cellulases. The production of β-glucosidase by this fungus being however very low, its enzymatic complex is supplemented with a β-glucosidase of fungal origin [WOODWARD and WISEMAN, Enzyme Microbiol. Technol., 4, 73–79, (1982); WILHEM and SHAM, Acta Biotechnol, 6, 2, 115–121, (1986)]. However, the inhibition of β-glucosidase by its reaction product, glucose, considerably reduces the efficiency of the method.

The use of enzymatic complexes of bacterial origin [ROMANIEC et al., Enzyme Microb. Technol., 9, 474–478, (1987)] has also been envisaged for the saccharification of cellulose. However, the problem of inhibition, by glucose, of the β-glucosidase activity also exists in this case [WOODWARD and WISEMAN, Enzyme Microbiol. Technol. 4, 73–79, (1982); WILHELM and SHAM, Acta Biotechnol, 6, 2, 115–121, (1986); KWON et al., FEMS Microbiology Letters, 149–154, (1992)].

Hydrolysis by β-glucosidase therefore constitutes a limiting step in enzymatic saccharification methods.

It would therefore be desirable, for all these applications, to have a β-glucosidase which is active in the presence of glucose, so as to be capable of being used in media high in glucose.

The inventors have now detected in filamentous fungi, such as *A. niger* and *A. oryzae*, a β-glucosidase whose activity is only very weakly inhibited by glucose, and have succeeded in producing, purifying and characterizing this enzyme so as to use the properties thereof.

The subject of the present invention is a purified preparation of β-glucosidase of fungal origin, called hereinafter BGII, characterized in that it is an exocellular β-glucosidase, capable of being obtained from filamentous fungi, whose molecular mass, estimated by exclusion chromatography, is about 30,000, the isoelectric point, determined by electrofocusing, is about 4.2, the optimum pH is between 4.5 and 6.0, the inhibition constant (Ki) for glucose is about 950 mM, and which retains its full activity after incubating for 24 hours at pH 3.0 and at 20° C.

The β-glucosidase BGII obtained in accordance with the invention is also less inhibited than other β-glucosidases by δ-gluconolactone.

According to a preferred embodiment of the present invention, the β-glucosidase BGII is capable of being obtained from a filamentous fungus chosen from the group consisting of A. niger and A. oryzae. These filamentous fungi are GRAS (Generally Recommended As Safe).

Depending on the medium on which they are cultured, these fungi produce a larger or smaller quantity of β-glucosidase BGII. The inventors have, for example, observed that the use of a medium containing quercetin as carbon source was particularly advantageous for the purpose of increasing the yield of β-glucosidase BGII.

β-Glucosidase BGII is stable in a wide pH and temperature range and can therefore be used in very diverse media. It has a broad activity spectrum and allows the hydrolysis of β-D-glucosides of various types. Furthermore, it is exocellular, which facilitates its production.

Because of these characteristics, the use of β-glucosidase BGII can be envisaged in all cases where it is desired to carry out the hydrolysis of β-D-glucosides in media containing glucose, such as for example:

in order to increase the flavor in fruit juices, by virtue of the hydrolysis of the glycosidic flavour precursors;

in order to improve the method of debittering citrus juices, by increasing the efficiency of the hydrolysis of naringin;

for the hydrolysis of toxic cyanogenetic glucosides, in particular in methods for the detoxification of cassava.

It can also be used for the synthesis of alkyl glucosides which are capable of being used, in particular, as detergents.

It can also be used to improve the methods for enzymatic hydrolysis of cellulose and of its derivatives.

β-Glucosidase BGII can be used in the form of a purified preparation, or in the form of a culture medium containing said enzyme; this medium can be used in the crude state, or after any appropriate treatment having the effect of increasing its BGII content.

The present invention will be understood more clearly with the aid of the additional description which follows, which refers to examples of production, purification and use of the β-glucosidase in accordance with the invention.

It should be understood, however, that these examples are given solely by way of illustration of the subject of the invention and do not constitute in any manner a limitation thereto.

EXAMPLE 1

Production of β-Glucosidase

The fungi A. niger 55465 and A. oryzae 12559 are obtained from the collection of the Centraalbureau Voor Schimmel Cultures (CBS, The Netherlands). The second strain of A. niger used is obtained from the laboratory collection. The fungi are preserved on a "Potatoes Dextrose Agar" medium.

The basic medium for the production of the enzyme contains the following compounds (% W/V): $(NH_4)_2HPO_4$: 0.3; $(NH_4)_2SO_4$: 0.8; $KH_2PO_4$: 0.1; $MgCl_2.6H_2O$: 0.1, Tween 80: 0.15. This medium is sterilized for 25 minutes at 120° C.

Moreover, the media containing the carbon sources to be tested (rutin, quercetin, cellobiose) are sterilized (120° C., 25 minutes) separately, and then mixed with the basic medium at a final concentration of 0.3% (W/V).

The cultures, after inoculation with the chosen fungus, are carried out at 30° C., with stirring (120 revolutions/minute). At various times during the culture, samples are taken in order to monitor the production of the enzyme. The culture medium collected and [sic] first centrifuged (5000 g, 10 minutes, 5° C.). The supernatant obtained, after dialysis, is used for the assay of the β-glucosidase activity.

The assay of the β-glucosidase activity is carried out by incubating, for 20 minutes at 40° C., 1 volume of enzymatic sample with 1 volume of p-nitrophenol β-D-glucoside (PNPG) (4 mM in 100 mM acetate buffer, pH 4.4). The quantity of PNP (pnitrophenol) liberated is estimated by adding 6 volumes of 0.1 M $Na_2CO_3$ and monitoring the absorbance reading at 400 nm. The enzymatic activity is expressed in nanokatals per ml (nkat/ml) of enzymatic solution. One nanokatal corresponds to the number of nanomoles of PNP liberated per second under the abovementioned conditions.

Various culture media were produced by varying the strain of filamentous fungi GRAS and the carbon source. The production of exocellular β-glucosidase, estimated by the hydrolysis of PNPG, was monitored during the development of the fungus. When the maximum enzyme production was achieved, the culture medium was centrifuged and the supernatant was concentrated on an AMICON® cell (10,000 cut-off).

Figure 1:
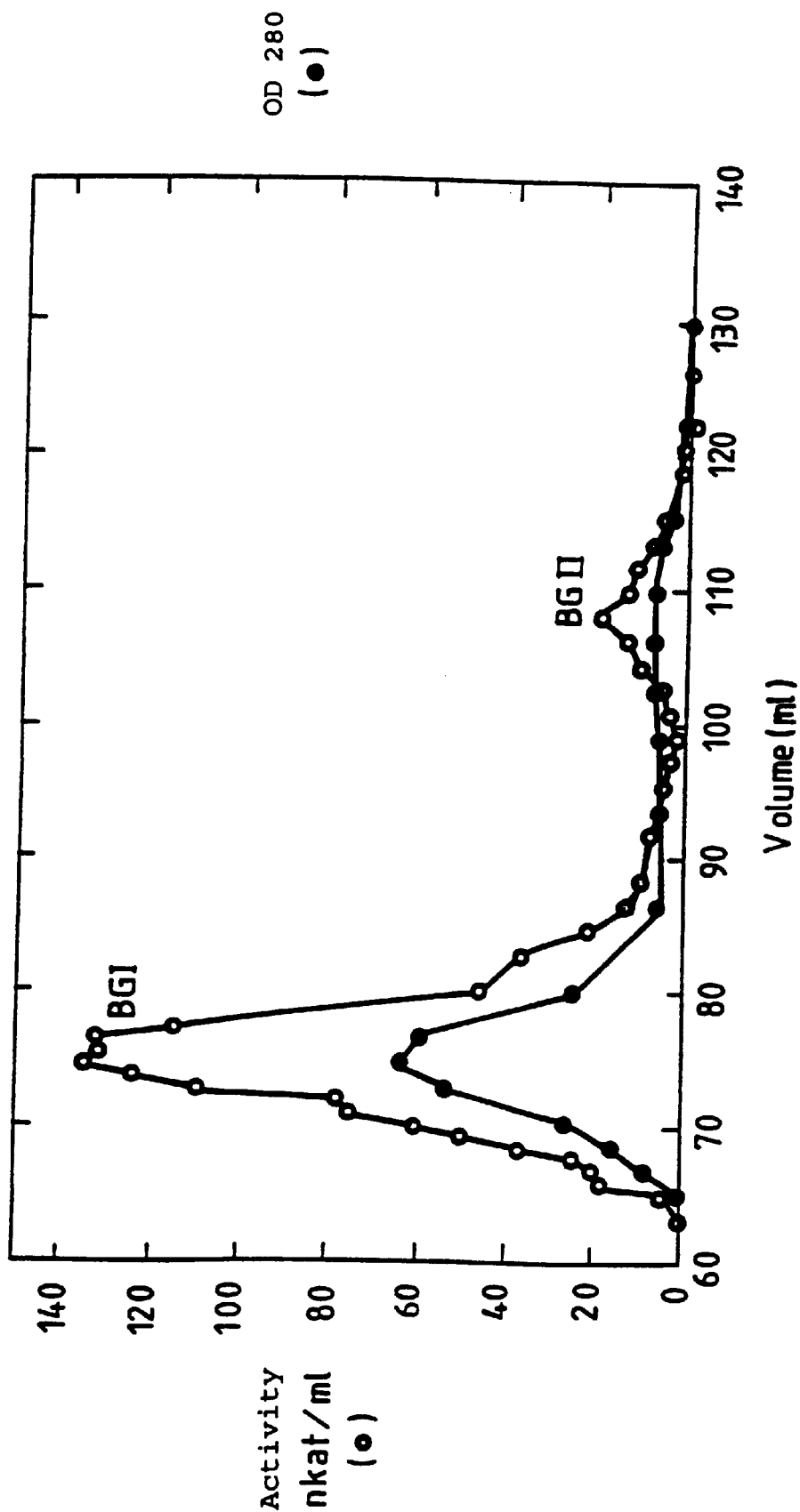
FIG. 1: Exclusion chromatography on ULTROGEL AcA44 of concentrated culture medium, harvested after culturing A. oryzae on quercetin.

Exclusion chromatography on ULTROGEL® AcA 44 made it possible to separate two clearly distinct β-glucosidase activity peaks designated: BGI and BGII (FIG. 1). In the case of all the culture media, the BGI and BGII elution volumes were identical.

The proportions of BGI and BGII obtained from 3 different strains of fungi cultured on quercetin, used as carbon source, are given in Table I below. The percentage of β-glucosidase activity is calculated from BGI and BGII fractions pooled after chromatography on ULTROGEL® AcA 44.

Table II illustrates the influence of the carbon source on the production of BGI and of BGII by A. oryzae.

TABLE I

| Strains | BGI (%) | BGII (%) |
|---|---|---|
| A. niger (INRA) | 96 | 4 |
| A. niger (CBS, 55465) | 97 | 3 |
| A. oryzae (CBS, 12559) | 90 | 10 |

BGII is produced by the three strains, the strain A. oryzae having, however, a higher yield.

TABLE II

| C source | BGI and BGII (nkat/l)* | BGI (%) | BGII (%) |
|---|---|---|---|
| Cellobiose | 820 | 99 | 1 |
| Rutin | 746 | 98 | 2 |
| Quercetin | 620 | 91 | 9 |

*in a culture medium.

Among the carbon sources used, it is quercetin which allows the maximum production of BGII compared with BGI.

In the work which follows, A. oryzae, cultured on quercetin, was chosen for the production of BGII and for studying the properties of the enzyme.

EXAMPLE 2

Purification and Characterization of β-Glucasidase BGII

The culture medium (3 liters), obtained after [lacuna] A. oryzae on quercetin and then concentrated, was subjected successively to two purification steps: exclusion chromatography and ion-exchange chromatography.

Exclusion chromatography

The culture medium (3 liters), harvested after culturing A. oryzae on quercetin, is first concentrated on an AMICON® cell (10,000 cut-off). It is then loaded onto a column (1.6×90 cm) filled with ULTROGEL® AcA44 (IBF) and previously equilibrated with a 100 mM phosphate-citrate buffer, pH 7.0, at 4° C. The elution is carried out with the same buffer at a flow rate of 7 ml/hour. The assaying of β-glucosidase activity and the estimation of proteins at 280 nm are performed on the fractions collected. The fractions corresponding to the second β-glucosidase activity peak (BGII) are combined.

Ion-Exchange Chromatography

The BGII fractions combined at the end of the exclusion chromatography are dialyzed against 25 mM imidazole buffer pH 7.4 and loaded onto a DEAE SEPHAROSE® CL6B column (1.6×26 cm) (PHARMACIA), previously equilibrated with this same buffer. A linear NaCl gradient from 0 to 0.5 M in the same buffer is prepared. The flow rate is 30 ml/hour. The fractions containing BGII are pooled.

Results

Exclusion chromatography on ULTROGEL® AcA44 showed two clearly distinct β-glucosidase activity peaks BGI and BGII (FIG. 1).

Figure 2:
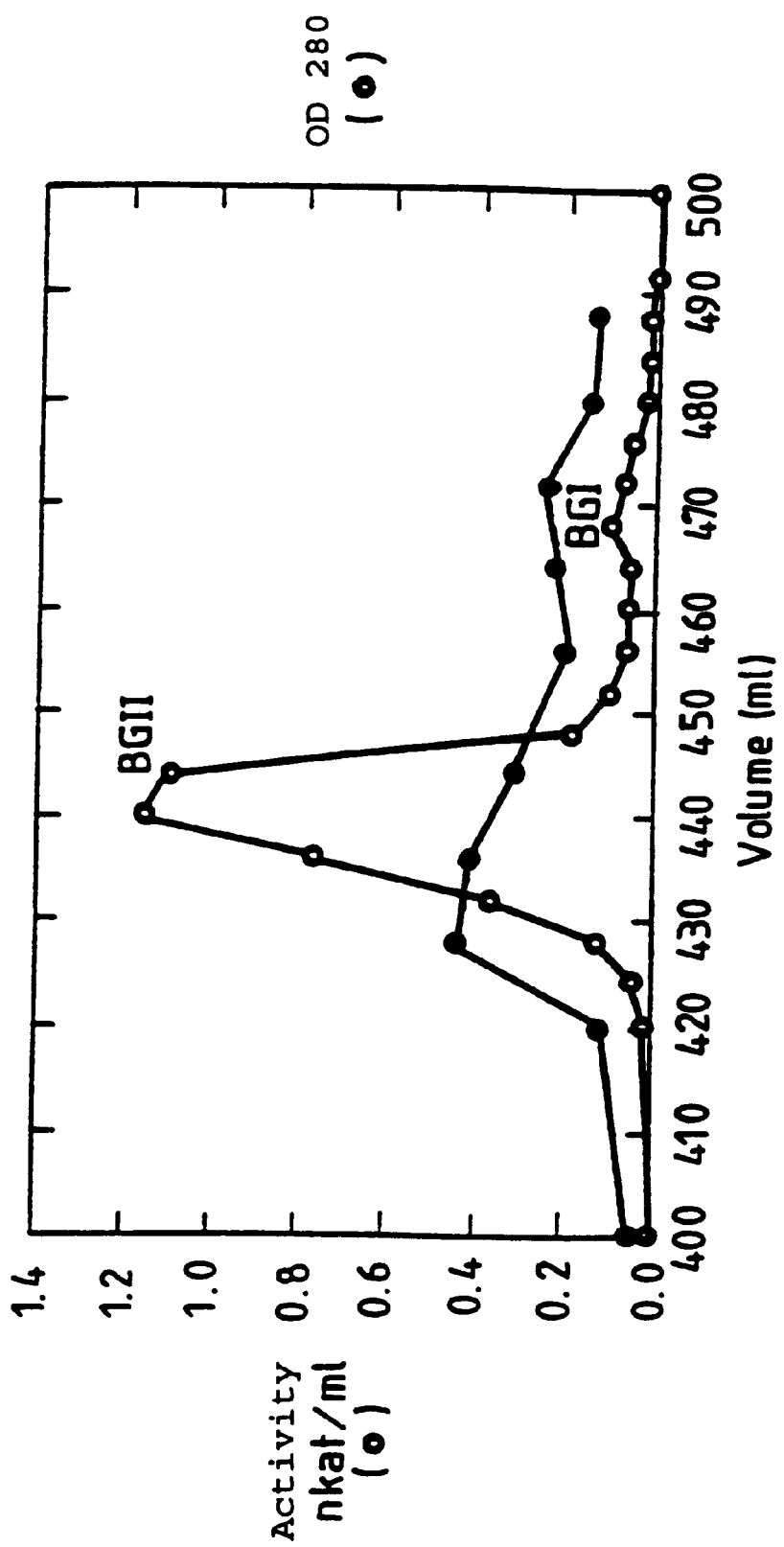
FIG. 2: Ion exchange chromatography on a DEAE SEPHAROSE CL6B of BGII fractions obtained from exclusion chromatography.

Ion-exchange chromatography on a DEAE SEPHAROSE® CL6B column of fractions high it possible to isolate BGII from BGI. BGII was eluted at an NaCl concentration of 0.17 M, followed by BGI which is eluted at 0.21 M NaCl (FIG. 2).

Estimation of the Molecular Mass

Proteins of known molecular mass are injected successively onto the ULTROGEL® AcA44 column in order to calibrate the column: cytochrome C(12,500), chymotrypsin (25,000), ovalbumin (45,000), serum of ovalbumin (68,000), lipoxygenase (100,000). The dead volume of the column is determined by injecting a solution of Blue Dextran.

The molecular mass of BGII, estimated by exclusion chromatography and with the aid of the proteins of known molecular masses, is around 30,000 (BGI is excluded from the fractionation range of the gel used, which indicates that it must have a molecular mass greater than 130,000). It should be noted that the molecular mass of most β-glucosidases of fungal origin which is known is often greater than 80,000. Fairly low molecular masses, namely 48,000 for β-glucosidase of C. guilliermondii and 41,000 for that of A. fumigatus have, however, been reported [WOODWARD and WISEMAN, Enzyme Microbiol. Technol., 4, 73–79, (1982)].

pH for Optimum Activity

The enzymatic solution is incubated for 20 minutes at 40° C. in a range of 100 mM phosphate-citrate buffer of pH varying from 2.5 to 8, in the presence of PNPG. The enzymatic activity is assayed according to the protocol described above.

Figure 4:
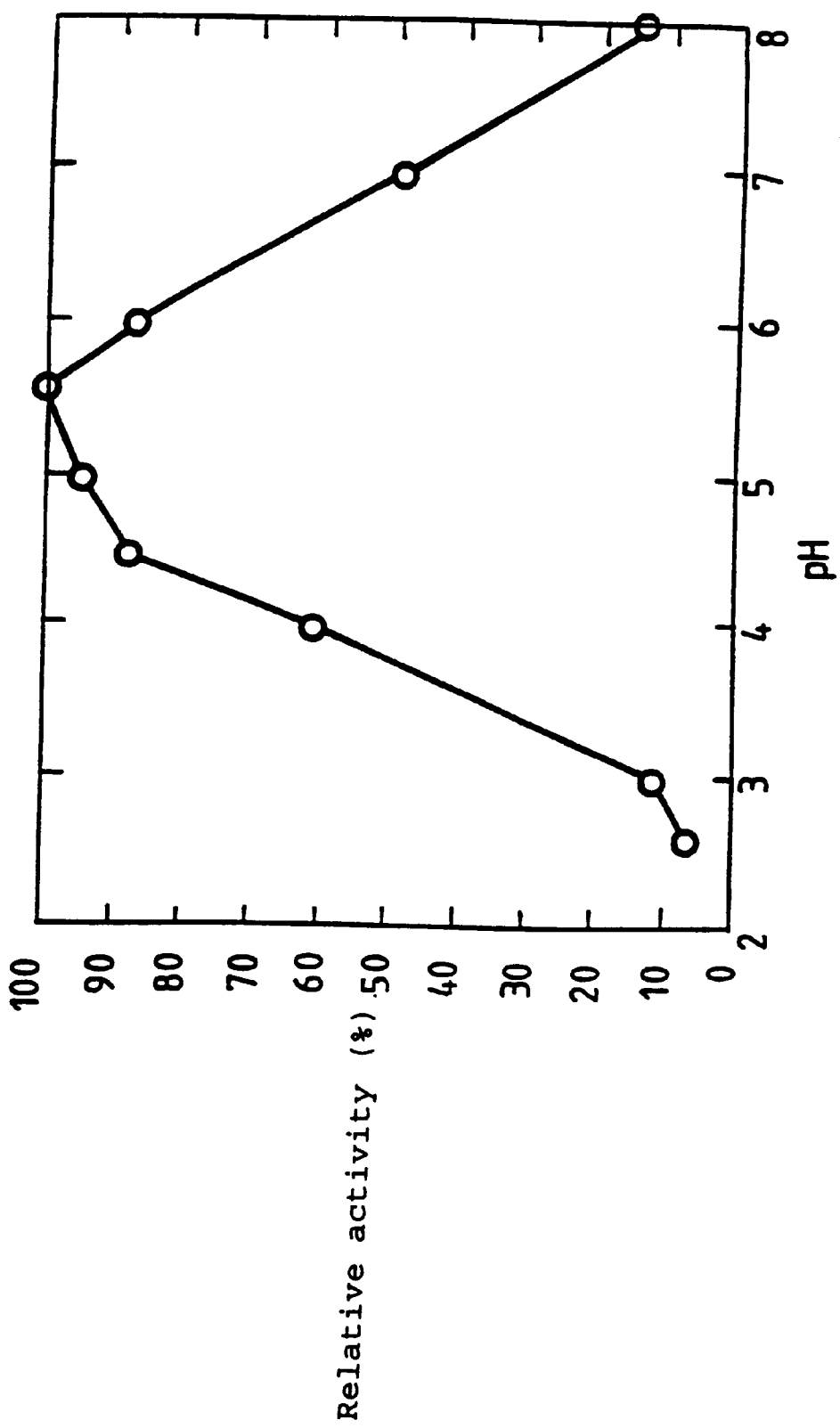
FIG. 4: Optimal pH of BGII activity.

The enzyme has an optimum pH of between 4.5 and 6.0 (FIG. 4), close to the values for known fungal β-glucosidases [GUNATA et al., Progress in Flavour Precursor Studies; SCHREIER, P., WINTERHALTER, P., Eds, Allured: Wheaton (USA), 219–234 (1993)]. The enzyme, like the known β-glucosidases of fungal origin, retains about 10% of its maximum activity at pH 3.0.

pHi of the Enzyme

The pHi of BGII was determined by isoelectrofocusing on agarose gel (gel thickness 1 mM [sic], 1% agarose, 12% sorbitol, pharmalyte 2.5–5.0). The apparatus used is the "LKB 2117 Multiphor II Electrophoresis Unit". After electrofocusing (1920 volts applied), BGII was located on the gel using, as substrate, 4-methylumbelliferyl-β-D-glucoside. The pHi of the enzyme was estimated at 4.2 by comparing its migration with that of the pHi markers.

Stability as a Function of the pH

The enzymatic solution is incubated for 24 hours at 20° C. in phosphate-citrate buffer solutions at the respective pH values of: 3.0, 6.0 and 7.0. The incubation media are then dialyzed against 100 mM acetate buffer pH 4.4. The measurements of activity, using PNPG as substrate, are carried out as described above.

The known glycosidases of filamentous fungi, such as for example that of A. niger distinguish themselves by a very good stability to the acidic pH of grape must (about 3.0), whereas those of S. cerevisiae, of C. wickerhamii and of grapes rapidly lose their activity at this pH [GUNATA et al., Progress in Flavour Precursor Studies; SCHREIER, P., WINTERHALTER, P., Eds, Allured: Wheaton (USA), 219–234, (1993); DELCROIX et al., Am. J. Enol. Vitic., 45, 3, p. 291–296 (1994)].

The BGII preparation derived from ion-exchange chromatography can be kept for 24 hours at 20° C., in a 100 mM phosphate-citrate buffer at each of the pH values 3.0, 6.0 and 7.0, remaining stable and without any loss of activity.

Likewise, the enzyme BGII added to a grape must at pH 2.9 and left at 20° C. still retains most of its activity one week later.

Inhibition by Glucose or δ-gluconolactone

The reaction medium containing an enzymatic solution to be tested (BGI, BGII or β-glucosidase of A. niger purified from the KLERZYME® (GIST-BROCADES, SECLIN, FRANCE) enzymatic preparation, which hydrolyzes terpenic glycosides during the making of dry wine [GUNATA et al., J. Inter. Sci. Vigne Vin, 24, 3, p. 133–143, (1990)] and which is used here by way of comparison) and a solution of PNPG at 4 mM is supplemented with a glucose or gluconolactone solution at various concentrations. The residual enzymatic activity is estimated after incubating the mixture for 20 minutes at 40° C.

The inhibition constant, for glucose, for the activity of BGI, BGII and KLERZYME® β-glucosidase, and the type of inhibition, are determined by the Lineweaver-Burk representation.

Results

Inhibition by Glucose

At the end of the exclusion chromatography, the study of the inhibition, by glucose, of the BGI and BGII activity (using PNPG as substrate), shows a notable difference between these two enzymes.

BGI, like practically all β-glucosidases of filamentous fungi [WOODWARD and WISEMAN, Enzyme Microbiol. Technol., 4, p.73–79 (1982); ARYAN et al., Am. J. Enol. Vitic., 38, p. 182–188, (1987); SHOSEYOV et al., Phytochem., 27, 7, p. 1973–1976, (1988); GUNATA et al., Progress in Flavour Precursor Studies; SCHREIER, P., WINTERHALTER, P., Eds, Allured : Wheaton (USA), 219–234, (1993)] is strongly inhibited by glucose.

Figure 3:
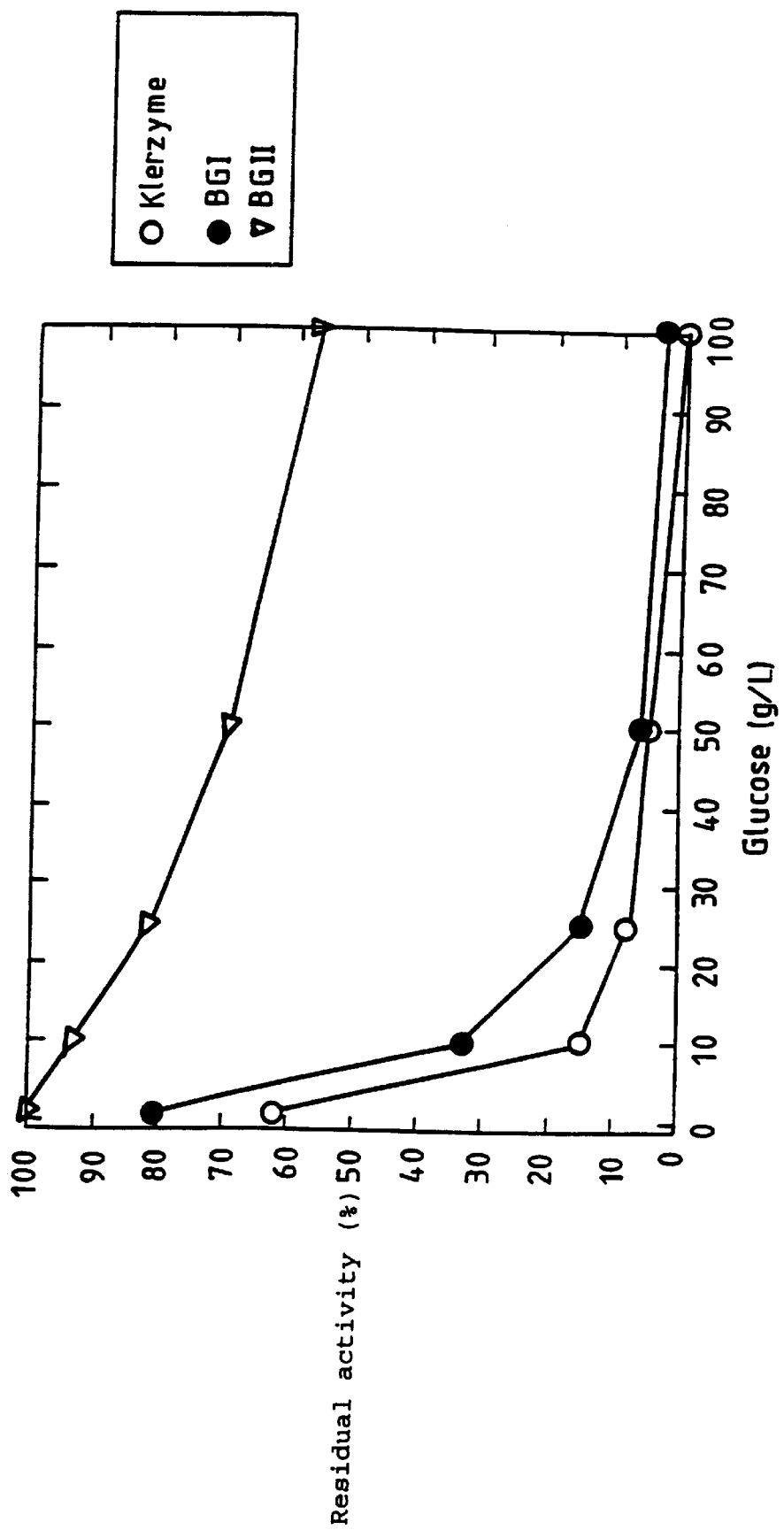
FIG. 3: Inhibition of the BGI, BGII, and KLERZYME activity in the presence of glucose using PNPG as a substrate.

In the presence of 25 g/l of glucose, there remains only about 15% of the activity of BGI and 10% of that derived from KLERZYME®, whereas BGII still retains about 80% of its activity. The latter enzyme is inhibited by only 57% in the presence of 100 g/l of glucose, the maximum content in a grape must intended for technological treatment, whereas BGI and the KLERZYME® β-glucosidase are practically completely inhibited at 50 g/l of glucose (FIG. 3).

At the end of the ion-exchange chromatography, the values for inhibition of BGII by glucose are of the same order as those obtained after exclusion chromatography.

The inhibition constants (Ki), for glucose, for the activities of BGI, of BGII and of KLERZYME® β-glucosidase were respectively calculated with respect to PNPG from the LINEWEAVER-BURK representation. Glucose behaves in the three cases like a competitive inhibitor. The inhibition constants are 3.2, 3.5 and 953 mM respectively for KLERZYME®, BGI and BGIIβ-glucosidases. The values obtained for the first two enzymes are close to those found for most β-glucosidases of filamentous fungi [GUNATA et al., Progress in Flavour Precursor Studies, SCHREIR, P., WINTERHALTER, P., Eds, Allured : Wheaton (USA), 219–234, (1993); KWON et al., FEMS Microbiology Letters, p. 149–154, (1992)].

On the other hand, a Ki value as high as that obtained for BGII has never been reported. Considerably lower values have been respectively found in the β-glucosidase of grapes, sweet almond and *Candida wickerhamii*, 170, 210, 230 mM [GUNATA et al., (1993) already cited].

Inhibition by δ-gluconolactone

Gluconolactone, produced from glucose by the action of glucose oxidase of fungi developed on grape berry, is known as an inhibitor, which is even more potent than glucose, of the activity of β-glucosidase [GUNATA et al., Progress in Flavour Precursor Studies, SCHREIR, P., WINTERHALTER, P., Eds, Allured: Wheaton (USA), 219–234, (1993)]. The concentration of gluconolactone may be as high as 2 g/l in the grape musts obtained from grapes attacked by fungi, such as Botrytis cinerea.

BGI and KLERZYM® β-glucosidase are already practically completely inhibited at a concentration of 1 g/l of gluconolactone. On the other hand, BGII still retains more than 30% of its activity at 1 g/l of gluconolactone, and 20% of its activity at 10 g/l of this compound.

Activity Spectrum

The activity of the BGII enzyme towards cellobiose, naringin and the β-D-glucosides of geraniol, nerol, linalol, benzyl alcohol and phenylethyl alcohol is studied in a buffered medium (100 mM acetate buffer pH 4.4) incubated at 40° C. The final concentration of each substrate is 2 mM in the reaction medium.

The hydrolysis of the substrates is estimated by thin-layer chromatography (TLC). The chromatography is carried out on a silica gel with the following solvent mixture: ethyl acetate=65, isopropanol=30, water=10 V/V/V. The compounds are revealed at 110° C. after the application of a 0.2% solution of naphthoresorcinal in an ethanol-sulfuric acid solution (19/1 V/V).

The hydrolysis, by BGII and by KLERZYME® β-glucosidase, of the β-D-glucoside of geraniol (1.5 mM) in a buffered medium (100 mM acetate buffer pH 4.4) in the presence of 100 g/l of glucose, as well as that of the β-D-glucosides of linalol, nerol and geraniol incorporated (0.15 mM of each) into a grape must (UGNI BLANC), by these same two enzymes were estimated by High-Performance Liquid Chromatography (HPLC).

A graft silica column C18, 5 µM (220×4.6 mM; Brownlee), and an acetonitrile/water mixture (30/70 V/V) in isocratic, with a flow rate of 1 ml/minute, were used respectively as stationary phase and as mobile phase. The sample is injected directly onto the column without prior treatment. The detection is made at 200 nm.

Results

BGII catalyzes the hydrolysis of the various substrates which were tested, namely aryl-(PNPGs), and alkyl glucosides (β-D-glucosides of geraniol, nerol, linalol, benzyl alcohol, phenylethyl alcohol), and a diglucoside (cellobiose), and it therefore behaves like the β-glucosidases of filamentous fungi [WOODWARD and WISEMAN, Enzyme Microbiol. Technol., 4 p. 73–79, (1982)].

Moreover, the hydrolysis of the glucoside of geraniol (1.5 mM=474 mg/l) in a buffered medium (acetate buffer, pH 4.4, 100 mM) in the presence of 100 g/l of glucose, by BGII (1.5 nkat/ml), and, by way of comparison, by KLERZYME® β-glucosidase (1.5 nkat/ml) was studied. After incubating for 24 hours at 20° C., the media are analyzed by HPLC. Half of the substrate was hydrolyzed by BGII, whereas only 9% of the glucoside disappeared through the action of KLERZYME® β-glucosidase.

In order to compare the efficacy of these two enzymes in a natural medium, a neutral must (UGNI blanc, pH 2.9, 90 g/l glucose), low in terpenic monoglucosides, but previously enriched with β-D-glucosides of linalol, nerol, geraniol, (0.15 mM of each) was supplemented either with BGII (0.6 nkat/ml), or with KLERZYME® β-glucosidase (0.6 nkat/ml). The amount of monoglucosides added to the must exceeds 10 times the amounts encountered in the musts of vines with the highest levels of these compounds. The media were analyzed by HPLC after incubating for one week at 20° C. Under these conditions, the KLERZYME® β-glucosidase had no effect on the substrates, whereas under the action of BGII, about 50% of the glucosides of nerol and of geraniol and 90% of the glucoside of linalol had disappeared.

The hydrolysis of naringin (naringenin-7-rhamnoglucoside) was also studied by thin-layer chromatography. It is known that the complete hydrolysis of naringin requires the successive action of an α-rhamnosidase and of a β-glucosidase.

As expected, BGII alone therefore had no action on naringin. The reaction medium was then supplemented with an α-rhamnosidase isolated from an enzymatic preparation (GUNATA et al. 1988), which cut the interglycoside bond, and liberated the naringenin monoglucoside. This monoglucoside was then completely hydrolyzed by BGII.

We claim:

1. A purified preparation of β-glucosidase, which is exocellular β-glucosidase obtained from filamentous fungi, whose molecular mass, estimated by exclusion chromotography, is about 30,000, the isoelectric point, determined by electrofocusing, is about 4.2, the optimum pH is 4.5 to 6.0, the inhibition constant (Ki) for glucose is about 950 mM, and which retains its full activity after incubating for 24 hours at pH 3.0 and at 20° C.

2. The purified preparation of β-glucosidase of claim 1, which is obtained from a filamentous fungus chosen from the group consisting of *A. niger* and *A. oryzae*.

3. A method for debittering citrus juice, which comprises a step during which the naringenin monoglucoside resulting from the prior action of an α-rhamnosidase on the naringenin present in said citrus juice is hydrolyzed by the purified preparation of β-glucosidase of claim 1.

4. A method for the enzymatic hydrolysis of cellulose and of its derivatives, which comprises a step which the cellobiose, resulting from the prior action of at least one cellulase, is hydrolyzed by the purified preparation of β-glucosidase of claim 1.

5. A process for enzymatic hydrolysis of β-D-glucoside or a mixture of β-D-glucosides which comprises contacting said glucoside(s) with the purified preparation of β-glucosidase of claim 1.

6. A process for the hydrolysis of a toxic cyanogenetic glucoside or mixtures thereof which comprises contacting said glucoside(s) with the purified peparation of β-glucosidase of claim 1.

7. A process for the production of alkyl glucosides which comprises contacting the β-D-glucoside precursor of said alkyl glucosides with the purified preparation of β-glucosidase of claim 1.

8. A method for hydrolyzing β-D-glucosides contained in fruit juice which comprises contacting said juice with the purified preparation of β-glucosidase of claim 1.

9. The method of claim 8, wherein the β-D glucosides are flavor precursors.

10. A purified preparation of β-glucosidase as in claim 1, obtained from the filamentous fungus.

11. A method of making the β-glucosidase of claim 1, comprising culturing a filamentous fungus which produces β-glucosidase in a culture medium and then isolating the β-glucosidase from the culture.

12. The method of claim 11, wherein the culture medium contains quercetin.

* * * * *